United States Patent [19]

Hervas

[11] Patent Number: 5,076,679
[45] Date of Patent: Dec. 31, 1991

[54] METHOD OF USING A MICROSCOPIC PREPARATIONS MARKER

[76] Inventor: Pedro L. Hervas, Paseo Santa María de la Cabeza 17., 28045 Madrid, Spain

[21] Appl. No.: 552,012

[22] Filed: Jul. 13, 1990

[30] Foreign Application Priority Data

Jul. 14, 1989 [ES] Spain .................................. 8902497

[51] Int. Cl.$^5$ ......................... G02B 21/34; G02B 7/16; B65H 37/00; B25H 7/04
[52] U.S. Cl. .................................... 359/381; 33/574; 221/73; 359/397; 359/900
[58] Field of Search .............. 350/520, 507, 321, 535, 350/320; 33/574; 221/73

[56] References Cited

U.S. PATENT DOCUMENTS

| | | | |
|---|---|---|---|
| 4,501,476 | 2/1985 | Reinheimer et al. | 350/520 |
| 4,690,521 | 9/1987 | Saccamanno | 350/520 |
| 4,762,405 | 8/1988 | Inoue et al. | 350/520 |
| 4,807,979 | 2/1989 | Saccamanno et al. | 350/520 |

Primary Examiner—Jon W. Henry
Attorney, Agent, or Firm—Cushman, Darby & Cushman

[57] ABSTRACT

A microscopic preparation marker includes a tape carrying a series of self-bonding marks which in use become preferentially bonded to the preparation. The device includes a spool with a supply of the marker-carrying substrate tape and another spool that drives the tape so that the tape leaves on the surface of the cover slide of the preparation, surrounding an area of interest that is to be later examined in more detail, a new mark each time the substrate tape is advanced and pressed against the cover glass. The device can be applied in scientific fields that use optical microscopes.

1 Claim, 3 Drawing Sheets

METHOD OF USING A MICROSCOPIC PREPARATIONS MARKER

BACKGROUND OF THE INVENTION

The invention relates to an instrument designed to mark particular parts of microscopic preparations, for scientific fields that use optical microscopes, such as in pathology and hematology laboratories.

In these fields of science, the preparations to be examined under the microscope are placed on a very thin glass called a slide, and covered by a very thin glass called a cover glass. If, in these preparations, there is an area that the researcher wants to mark for subsequent analysis, it is a conventional practice to draw a circle by hand with a felt pen, or using a device incorporated in the microscope's revolver, consisting of an ink cartridge with a fibre marker that draws circles; such a device has been the subject of a previous spanish patent application by the present inventor.

SUMMARY OF THE PRESENT INVENTION

The device that is the subject of the present invention, is placed inside the slide revolver of the microscope, and is pressed onto the preparation when there is an area to be marked. However, unlike the previous device, it does not use ink to mark a circle. Rather it comprises a different mechanism, one that incorporates a tape with self-bonding marks a respective one of which is placed on the glass each time that the device descends upon the area to be marked. After leaving a mark on the glass the tape automatically winds on with next the descending movement of the device, to leave a new mark.

This means and method for applying marks to microscope slide cover glasses avoids ink and all its bothers, such as drying, leaving stains, etc. . . It is a clean device, in which the number of marks that can be placed can be foreseen. For all these reasons, the device of the present invention is an important step forwards in the state of microscopic analysis technology.

BRIEF DESCRIPTION OF THE DRAWINGS

To facilitate a better understanding of the device, there follows a description which refers to the attached drawings, and wherein the preferred embodiment has been represented for a simply orientative and not limitative purpose.

In the Drawings.

DETAILED DESCRIPTION

Figure 1:
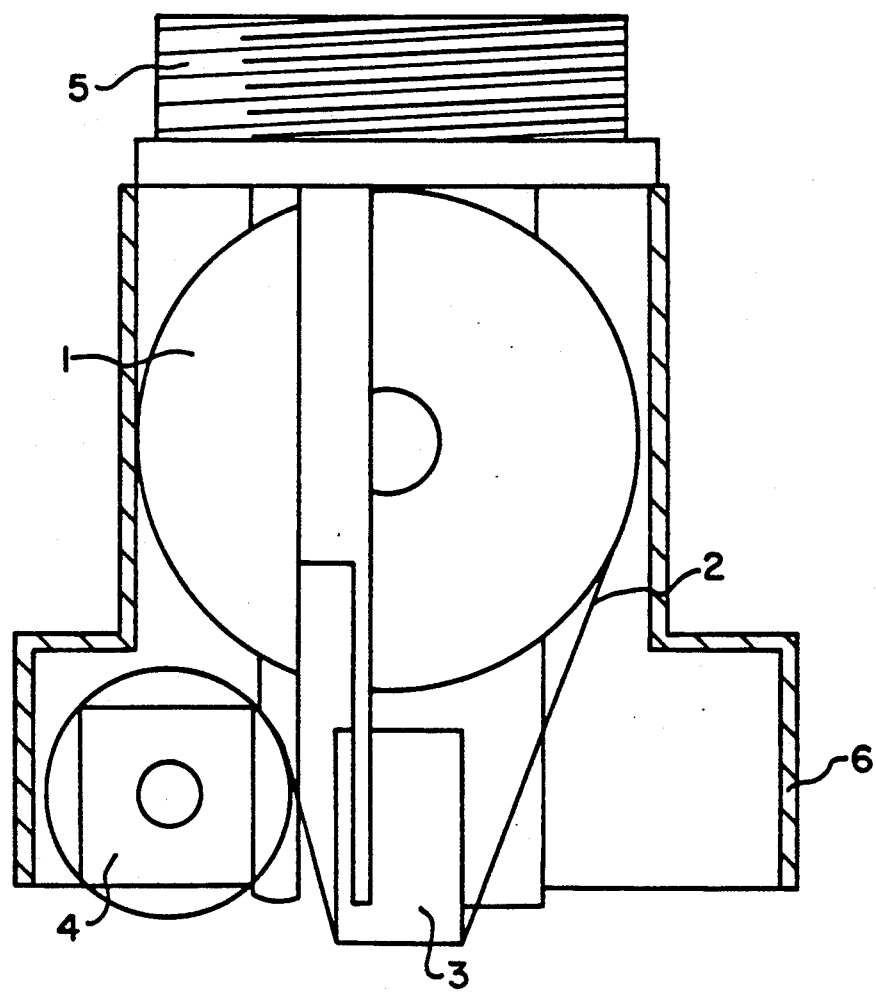
FIG. 1 is a diagrammatic front elevation view of a preferred embodiment of the marking device of the present invention, partly broken away and sectioned so as to expose internal features, and showing the marking tape in place.

In FIG. 1 a diagrammatic front view of the device can be seen, with a section of the external cover. According to this, the instrument includes a spool (1) to hold the tape (2) which has the self-bonding marks. The tape goes under the part (3) which is a cylinder that exerts pressure upon the tape and upon surface of the cover the glass on the preparation, that is being examined under the microscope thus causing the bonding of the mark onto the glass.

The tape (2) is driven by a second spool (4) which incorporates some engaging in a series of pivots (i.e., sprocket pins) that secure the tape by some equidistant holes made in the substrate tape (2).

The whole unit is screwed on to the slide revolver of the microscope instead of an objective, by the threading at the top (5) and the unit has an outer casing (6) which is lowered by hand onto the preparation to be marked. As the casing (6) is lowered set of spools, tape and marking cylinder are lowered with it.

Figure 2:
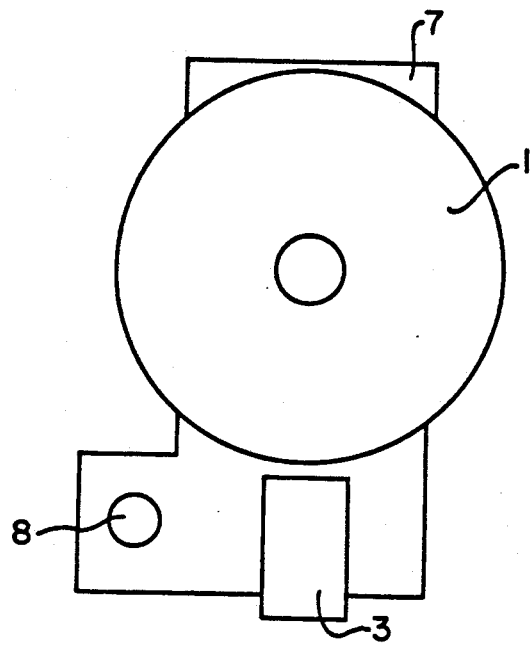
FIG. 2, is a front elevation view of one part of the device of FIG. 1.
Figure 4:
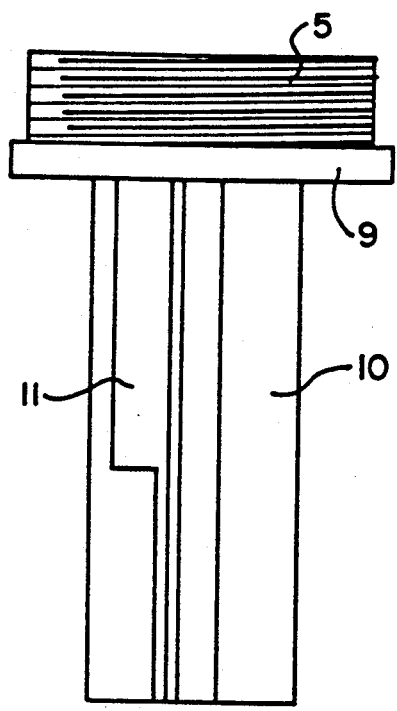
FIG. 4 is a front elevation view of another part of the device of FIG. 1.
Figure 3:
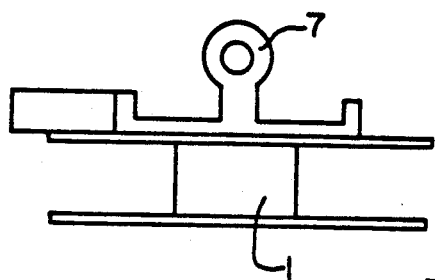
FIG. 3 is a diagrammatic bottom plan view of the part shown in FIG. 2.
Figure 5:
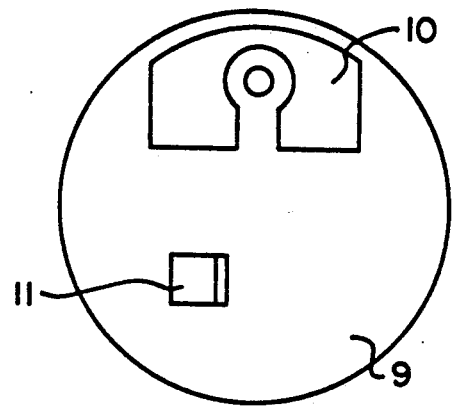
FIG. 5 is a bottom plan view thereof.
Figure 6:
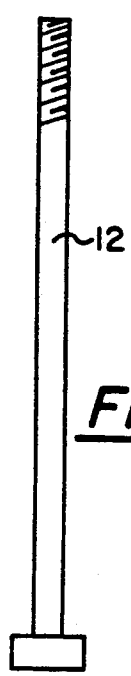
FIG. 6 is an elevation view of the axle on which the part shown in FIGS. 2 and 3 is slidably mounted.

FIGS. 2 and 3 respectively show a front view and a top plan view of a part (7) that incorporates the spool (1) that holds the tape marking (which has temporarily carried thereon the series of marking circles that are to be transferred to and become self-bonded to the microscope slide cover glass) the marking cylinder (3) and the axle (8) on which the sprocket toothed spool that drives the tape (2) is held. This part (7) slides along the part represented in FIG. 3, in front view in FIG. 4 and in bottom plan view in FIG. 5. This fixed part (9) includes the threaded mounting collar (5) which is used for attachment of the device to the microscope revolver, and slot (10) where the corresponding shape of part (7) slides. Also outline (11) in which the elastic strip that turns the driving spool (4) is placed to turn the spool when it comes down. FIG. 6 shows the screw (12) that, attached to the upper side of the fixed part (9), forms the axle upon which part (7) slides. The screw (12) is covered by a spring that brings part (7) back up again once the pressure exerted to mark the preparation (by transferring a circular marker from the tape to the surface of the cover slide) is released.

Figure 7:
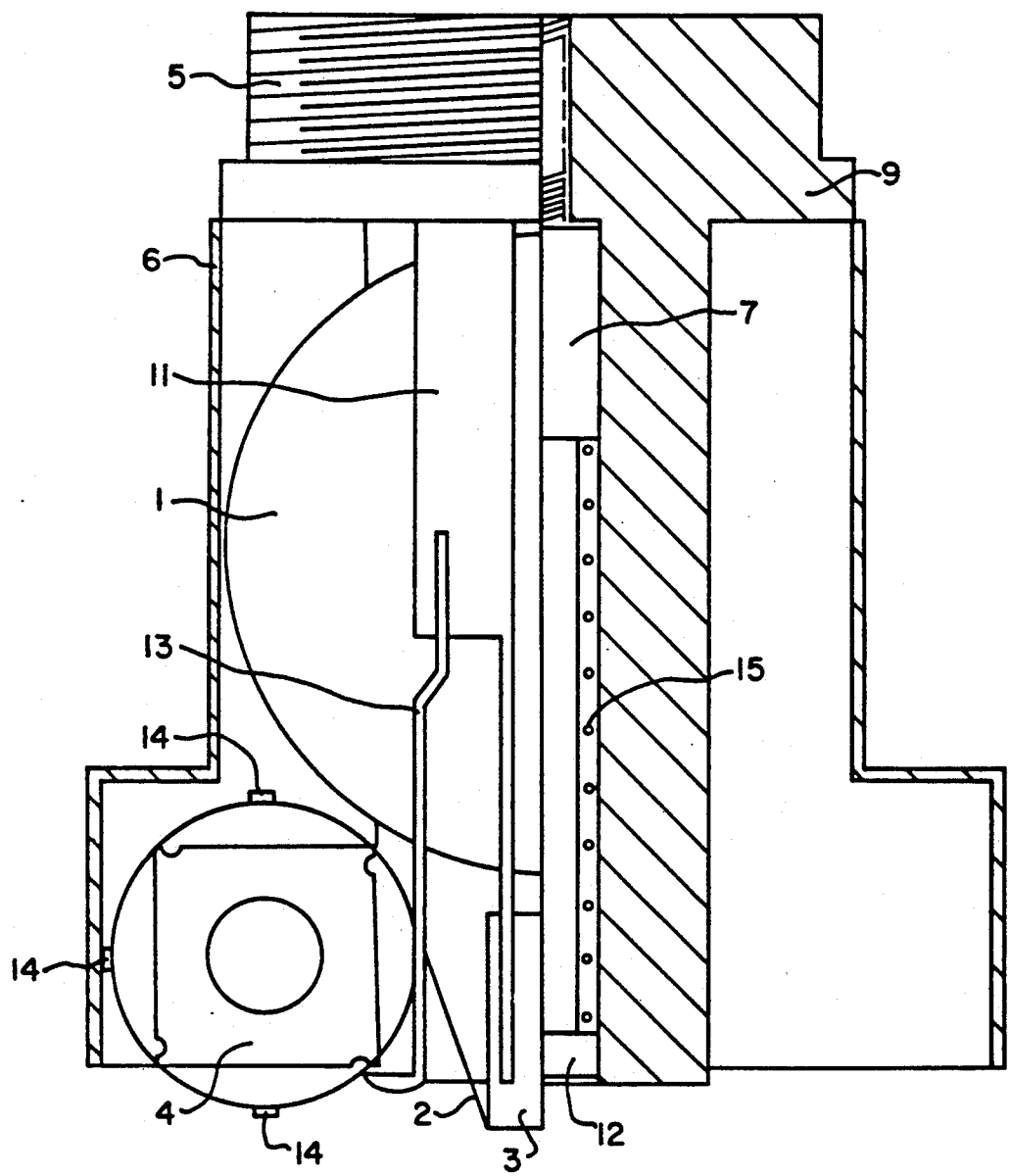
FIG. 7 is a larger scale view of the structure shown in FIG. 1.

FIG. 7 shows a front view of the unit, with cut away sections from which it can be seen how, when the casing (6) is lowered, the set-spools (1 and 4), marking cylinder (3) and tape (2)-fixed to part (7) is lowered. When the unit comes down, the driving spool (4) is pushed by the elastic strip (13) mounted on fixed profile (11); this forces the driving spool (4) to rotate one quarter of a turn, and this drives the tape (2) which has the series of self-bonding marks temporarily carried thereon, and the series drive sprocket holes in which the drive sprocket pins (4) engage, until the next mark is left on the glass, where it is bonded by pressure from cylinder (3), thereby preferentially adhering to the surface of the cover glass and becoming released from the substrate tape. When pressure on the casing (6) stops, the spring (15) returns the unit fixed to sliding part (7). A catch (not shown) makes it impossible to turn the driving spool (4) in the opposite direction, so that when the spool rises, it moves the elastic strip (13) sideways, and is then left in a position to impel a new rotation for the next operation.

Figure 8:
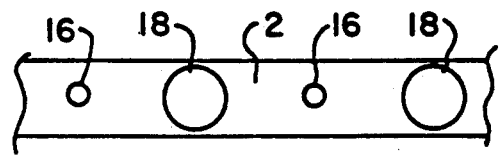
FIG. 8 is a bottom plan view of a piece of the marking tape.

FIG. 8 shows a piece of the substrate tape (2) that carries the self-bonding marks 16 and which also has the series of sprocket holes 18 that receive the drive sprocket teeth (14) of the driving spool (4).

I claim:

1. A method for marking areas on surfaces of microscopic preparations to identify areas for further study, comprising:

mounting a supply of circular marker-bearing tape to a slide revolver of a microscope, so as to extend along a path between a supply spool and a take-up spool;

at a site intermediate the supply and take-up spools, successively pressing the tape against a surface of a microscopic preparation, and, in conjunction with each such pressing, advancing the tape in order to bring a next marker into position to be pressed onto the surface; the tape on the supply spool and to said site carrying a series of prefabricated circular markers each adapted to detach from the tape and preferentially attach to said surface when the tape at said site is pressed against said surface.

* * * * *